United States Patent [19]

Chamness

[11] Patent Number: 5,547,989
[45] Date of Patent: Aug. 20, 1996

[54] COMPOSITIONS FOR TREATING CORNS AND CALLUSES

[75] Inventor: Thomas W. Chamness, Memphis, Tenn.

[73] Assignee: Schering-Plough Healthcare Products, Inc., Memphis, Tenn.

[21] Appl. No.: 304,009

[22] Filed: Sep. 9, 1994

Related U.S. Application Data

[63] Continuation-in-part of Ser. No. 293,369, Aug. 19, 1994, abandoned.

[51] Int. Cl.$^6$ .......................... A61K 31/20; A61K 31/19
[52] U.S. Cl. ............................. 514/558; 514/574
[58] Field of Search ....................... 514/558, 574

[56] References Cited

U.S. PATENT DOCUMENTS

| 4,386,104 | 5/1983 | Nazzano-Porro | 514/558 |
| 4,713,394 | 12/1987 | Thornfeldt | 514/574 |
| 4,895,727 | 1/1990 | Allan | 424/642 |

FOREIGN PATENT DOCUMENTS 0336880  11/1989  European Pat. Off. .

*Primary Examiner*—Kimberly Jordan
*Attorney, Agent, or Firm*—Matthew Boxer; John J. Maitner

[57] ABSTRACT

Topical compositions in gel form for the treatment of corns and calluses comprising a 7 to 13 carbon dicarboxylic acid and a pharmaceutically acceptable carrier, are described.

23 Claims, No Drawings

COMPOSITIONS FOR TREATING CORNS AND CALLUSES

RELATED APPLICATIONS

This application is a continuation-in-part pending application of Ser. No. 08/293,369 filed Aug. 19, 1994.

BRIEF SUMMARY OF THE INVENTION

The invention relates to topical compositions in gel form for treating corns and calluses which comprise a 7 to 13 carbon dicarboxylic acid such as $HO_2C(CH_2)_7CO_2H$, $HO_2C(CH_2)_8CO_2H$, $HO_2C(CH_2)_9CO_2H$, $HO_2C(CH_2)_{10}CO_2H$, $HO_2C(CH_2)_{11}CO_2H$, $HO_2C(CH_2)_6CO_2H$, $HO_2C(CH_2)_5CO_2H$, $HO_2C(CH_2)_2CHCH_3(CH_2)_3CO_2H$, $HO_2C(CH_2)_6(CHCH_3)CO_2H$,

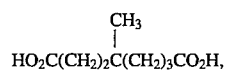

or most preferably azelaic acid; or a corresponding pharmaceutically acceptable salt or ester thereof in combination with a pharmaceutically acceptable carrier. The invention also relates to a method for treating the above-described conditions which comprises administering an effective amount of a 7 to 13 carbon dicarboxylic acid such as $HO_2C(CH_2)_7CO_2H$, $HO_2C(CH_2)_8CO_2H$, $HO_2C(CH_2)_9CO_2H$, $HO_2C(CH_2)_{10}CO_2H$, $HO_2C(CH_2)_{11}CO_2H$, $HO_2C(CH_2)_6CO_2H$, $HO_2C(CH_2)_5CO_2H$, $HO_2C(CH_2)_2CHCH_3(CH_2)_3CO_2H$, $HO_2C(CH_2)_6(CHCH_3) CO_2H$,

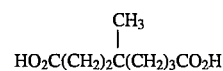

or most preferably azelaic acid; or a corresponding pharmaceutically acceptable salt or ester thereof.

DETAILED DESCRIPTION OF THE INVENTION

Hyperkeratotic tissues, such as: corns (heloma), and calluses (tyloma) are well defined, thickened lesions of the epidermis. They occur at skin sites that are normally involved in chronic mechanical stress (corns and calluses). Pain produced by the thickened tissue can cause these lesions to be debilitating.

Traditionally, "keratolytic agents", such as salicylic acid and resorcinol, have been applied topically to these lesions to solubilize intercellular bonds resulting in desquamation of the thickened, hyperkeratotic tissues.

The goal was to develop a faster acting corn and callus remover product. To achieve this goal a 7 to 13 carbon dicarboxylic acid, namely, azelaic acid was evaluated. Assays of keratinocyte differentiation and keratolytic action, as described below were employed to identify that azelaic acid and other compounds of the invention possess this activity.

The present invention provides new topical compositions for the treatment of all kinds of corns and calluses. The compositions of the invention are gels which localize the active ingredient at the treatment site on the corns or calluses. The compositions of the invention are also liquids which form films and thereby localize the active ingredient at the treatment site on the corns or calluses. The compositions of the invention are also plaster disks or pads which localize the active ingredient at the treatment site on the corns or calluses. The compositions of the invention provide for faster removal of corns, and calluses than do prior art compositions. The compositions of the invention can also be used in the treatment of hyperkeratinizing and hyperproliferative skin diseases and conditions such as ichthyoses, porokeratoses, follicular keratoses, palmoplantar keratodermas, psoriasis, eczema, dandruff and dry skin. The invention also relates to a method for treating the above-described medical conditions which comprises administering an effective amount of a 7 to 13 carbon dicarboxylic acid such as $HO_2C(CH_2)_7CO_2H$, $HO_2C(CH_2)_8CO_2H$, $HO_2C(CH_2)_9CO_2H$, $HO_2C(CH_2)_{10}CO_2H$, $HO_2C(CH_2)_{11}CO_2H$, $HO_2C(CH_2)_6CO_2H$, $HO_2C(CH_2)_5CO_2H$, $HO_2C(CH_2)_2CHCH_3 (CH_2)_3CO_2H$, $HO_2C(CH_2)_6(CHCH_3) CO_2H$,

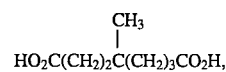

or most preferably azelaic acid; or a corresponding salt or ester thereof.

The topical compositions of the present invention can be gels which comprise a 7 to 13 carbon dicarboxylic acid such as azelaic acid; or a corresponding pharmaceutically acceptable salt or ester thereof. The topical compositions of the present invention can also be liquids which comprise a collodion film forming vehicle and which comprise a 7 to 13 carbon dicarboxylic acid such as azelaic acid; or a corresponding pharmaceutically acceptable salt or ester thereof as described above. The topical compositions of the present invention can also be alcoholic liquids which comprise a 7 to 13 carbon dicarboxylic acid such as azelaic acid; or a corresponding pharmaceutically acceptable salt or ester thereof. The topical compositions of the present invention can also be liquids which comprise a collodion film forming vehicle and which comprise a 7 to 13 carbon dicarboxylic acid such as azelaic acid; or a corresponding pharmaceutically acceptable salt or ester thereof as described above. The topical compositions of the present invention can also have as the pharmaceutically acceptable carrier a plaster disk, a plaster pad, a patch or a bandage and which further comprises a 7 to 13 carbon dicarboxylic acid such as azelaic acid; or a corresponding pharmaceutically acceptable salt or ester thereof as described above. As used herein, "a 7 to 13 carbon dicarboxylic acid" means a 7 to 13 carbon straight or branched chained dicarboxylic acids such as $HO_2C(CH_2)_7CO_2H$, $HO_2C(CH_2)_8CO_2H$, $HO_2C(CH_2)_9CO_2H$, $HO_2C(CH_2)_{10}CO_2H$, $HO_2C(CH_2)_{11}CO_2H$, $HO_2C(CH_2)_6CO_2H$, $HO_2C(CH_2)_5CO_2H$, $HO_2C(CH_2)_2CHCH_3 (CH_2)_3CO_2H$,

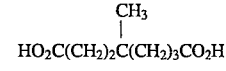

or a corresponding pharmaceutically acceptable salt or ester thereof. The preferred 7 to 13 carbon dicarboxylic acid of the invention is azelaic acid.

The chemical structure of azelaic acid is as follows: $HO_2C(CH_2)_7CO_2H$.

The topical compositions of the invention comprise a 7 to 13 carbon dicarboxylic acid and a pharmaceutical carrier material which forms a gel. The topical compositions of the invention also comprise a 7 to 13 carbon dicarboxylic acid wherein the pharmaceutical carrier material is a plaster pad or disk.

A composition in accordance with the invention comprises azelaic acid in a range of about 4 to about 64% (weight/weight).

More preferably, the topical compositions of the invention contain azelaic acid at a range of about 8 to about 40% (weight/weight).

Those skilled in the art will be able to maximize the safety and efficacy of a given formulation.

Topical compositions of the invention contain a pharmaceutically acceptable carrier. The pharmaceutically acceptable carrier delivers the active ingredient to the site of application. The pharmaceutically acceptable carrier may be a film former such as flexible collodion, USP. The pharmaceutically acceptable carrier may also contain a liquid such as propylene glycol, petrolatum, ethanol, acetone, dimethyl sulfoxide (DMSO), and the like provided, that the final form of the composition is a gel or a film. The pharmaceutically acceptable carrier may also be pad devices, disks or plaster.

Topical compositions of the invention may also contain a viscosity enhancer. Viscosity enhancers increase the viscosity of the composition so that it does not spread beyond the site of application. An example of a viscosity enhancer is Balsam Fir (Oregon).

Topical compositions of the invention may also contain a film former. When a film former dries, it forms a protective film over the site of application to prevent removal of active ingredient from the site. An example of a film former which may be used is Flexible Collodion, USP.

Topical compositions of the invention may also contain a colorant such as β-Carotene.

Liquid alcoholic compositions of the invention comprise vehicles such as Arlasolve 200L; Ceraphyl 230; or "88" Vehicle.

Topical compositions of the invention may also contain a solvent which serves to dissolve the active ingredient. An example of a solvent which may be used is acetone. As can be seen, the solvent may also sometimes serve as the carrier.

Current collodion-based FDA monograph approved formulas may be employed in such topical liquid compositions.

Alternatively, current plaster pad-type FDA monograph approved formulas may be used in devising compositions of the invention.

One skilled in the art would be able to devise a variety of suitable plaster pad-type formulations. Modified FDA monograph approved pad devices, disks or plaster may also be used as the carrier material. One skilled in the art would be able to apply a 7 to 13 carbon dicarboxylic acid of the invention to these pad devices, disks or plaster to form a composition of the invention.

In preparing topical compositions of the invention, there can be added conventional adjuvants such as propionic acid, salicylic acid, propylene glycol, acetone and lactic acid, conventional penetration enhancers such as erucic acid, oleic acid, and behenic acid; conventional buffers, preservatives, hydrophilic emulsifiers, lipophilic emulsifiers, sunscreening agents, perfumes, emollients, deodorants, humectants, and the like. Colorants may also optionally be added in the compositions of the invention.

In applying the gel formulations to the patient in need of such treatment, the gel formulations are applied, rubbed or spread on the affected area of the skin.

In applying plaster-pad formulations to the patient in need of such treatment, plaster-pad formulations are applied to the affected area of the skin so that the pad adheres to the skin. Similar application would be carried out for patch, bandage, or disk formulations.

Compositions of the invention are to be applied in a therapeutically effective amount. A "therapeutically effective amount" means any amount which will cause improvement in a disease condition (such as removal of a callus) when applied to the affected area repeatedly over a period of time. The amount will vary with the condition being treated and the concentration of the active ingredients in the formulation being applied. Appropriate amounts in any given instance will be readily apparent to those skilled in the art by routine experimentation.

Experiments were carried out which demonstrate that when azelaic acid is included in compositions, that the resulting composition is more effective in causing callus sloughing from guinea pig footpads, than salicylic acid alone. These experiments are described below.

Action of Azelaic Acid for Removal of Guinea Pig Footpad Callus: Description of Guinea Pig Footpad Assay (GPFA).

To evaluate keratolytic agents an animal model, GPFA, was developed. The analysis was performed according to the following protocol, using the guinea pig footpad as the test site. Three Hartley guinea pigs (250–400 g) were used per test group for in vivo evaluations. Either right or left footpads were treated with the opposite footpad as untreated control. For each treatment group, the same footpad was treated on each animal. The treated footpad received 200 μl of the test material saturated into a small cotton piedget. The cotton piedget was occluded with several wrappings of Blenderm tape (3m Corporation, St. Paul, Minn.) and finally secured from removal with a wrapping of Zonas tape (Johnson and Johnson, New Brunswick, N.J.). Each group of three animals was placed in a polycarbonate cage with contact bedding for 18–24 hours (overnight). At the end of the treatment period, the bandages were removed with surgical scissors and the footpads were examined for gross keratolytic effects or dermatotoxicity. Observations were carried out at daily intervals for one week. Clinical grades were recorded for possible keratolytic effects beginning on Day 2 and continuing through Day 7. Appropriate vehicle controls and bandage control groups were included in each experiment. Azelaic acid was prepared as a 12% (weight/weight) solution as described below.

The following gel formula for evaluating azelaic acid in the GPFA is a preferred composition of the invention.

| Component | Percentage of Formula % (weight/weight) |
| --- | --- |
| AZA | 12% |
| EtOH | 47% |
| Arlasolve 200 L | 39% |
| Klucel HF | 2% |

As used herein AZA means azelaic acid. Formulation of azelaic acid in Preferred Vehicle The azelaic acid formula was prepared as follows:

1) AZA and ariasolve were mixed.
2) Alcohol was added and the resulting material was mixed until the AZA was dissolved.
3) Klucel was added and mixing followed until the Klucel was dissolved and hydrated.
4) The composition made in step 3 was then transferred to appropriate containers for storage at room temperature ranging from about 22° to about 27° C.

| Liquid Formula for Evaluating Salicylic Acid (SA) in the GPFA. | |
| --- | --- |
| Component | Percentage of Formula % (weight/weight) |
| SA | 12.6 |
| Balsam Fir (Oregon) | 5.0 |
| β-Carotene, 22% in Vegetable Oil | 0.05 |
| Acetone | 10.0 |
| Flexible Collodion, USP | q.s. 100.0 |

The SA formula was prepared as follows:

1) Balsam fir (Oregon) was mixed with acetone in a suitable vessel.
2) β-Carotene, 22% in vegetable oil, was added to the solution prepared in step 1 and thoroughly mixed.
3) Flexible collodion, USP, was added to the solution prepared in step 2 and thoroughly mixed.
4) SA was added to the solution prepared in step 3.
5) The composition from step 4 was thoroughly mixed until the SA was completely dissolved.
6) The composition made in step 5 was then transferred to appropriate containers for storage at room temperature ranging from about 22° to about 27° C.

| Liquid Formula for Evaluating Azelaic Acid in the GPFA. | |
| --- | --- |
| Component | Percentage of Formula % (weight/weight) |
| Azelaic Acid | 12.00 |
| Balsam Fir (Oregon) | 5.0 |
| β-Carotene, 22% in Vegetable Oil | 0.01 |
| Acetone | 10.0 |
| Flexible Collodion, USP | q.s. 100.0 |

The Azelaic Acid formula was prepared as follows:

1) Balsam fir (Oregon) was mixed with acetone in a suitable vessel.
2) Flexible collodion, USP, was added to the solution prepared in step 1 and thoroughly mixed.
3) Azelaic Acid was added to the solution prepared in step 2.
4) The composition from step 3 was thoroughly mixed until the Azelaic acid was completely dissolved.
5) The composition made in step 5 was then transferred to appropriate containers for storage at room temperature ranging from about 22° to about 27° C.

The two compositions just above are film forming compositions of the invention.

The relative efficacy of keratolytic action of the compounds for removal of guinea pig foot pad callus was determined by the following clinical grading scale:

| Clinical Grade | Appearance of Footpad and Footpad Callus |
| --- | --- |
| 0 = | No visible difference, smooth feet, or equivalent to control. |
| 0.5 = | Slight fine cracks in skin visibly different from control. |
| 1 = | Somewhat larger cracks with edges turned up slightly. |
| 2 = | Obvious separation of stratum corneum (SC) over a limited area of the footpad. |
| 3 = | Separation of SC over a large area of the footpad. |
| 4 = | SC has peeled off completely revealing intact underlying epidermis, i.e., normal appearing skin. |

The clinical grades were then used to calculate a keratolytic efficacy score referred to as the Keratolytic Index (KI). The following formula is used to calculate the KI for a given test group.

$$KI = \frac{\text{Maximum Average Clinical Grade}}{\text{The Number of Days Until The Average Clinical Grade} \geq 2} \times 10$$

The KI scores achievable for this analytical method range from 0, no apparent keratolytic activity, to 20, maximum keratolytic action. The results of several experiments comparing the KI of azelaic acid with that of SA is given in Table 1 below. Azelaic acid clearly has a higher KI than salicylic acid under these test conditions. The average KI in control groups was less than 1. There was no evidence of dermatotoxicity caused by azelaic acid or SA in any of the assays that were conducted.

TABLE 1

Table 1: Keratolytic Indices (KIs) for Azelaic Acid and Salicylic Acid as determined in the Guinea Pig Footpad Assay(GPFA).

| Keratolytic Agents | Percent (w/w) of Keratolytic Agent in Formula[1] | KI[2] |
| --- | --- | --- |
| Experiment 1 | | |
| Salicylic Acid | 12.0% Collodion | 3.8 |
| Azelaic Acid | 12.0% Collodion | 12.2 |
| Experiment 2 | | |
| Azelaic Acid | 12.0% Ucare | 6.7 |
| Azelaic Acid | 12.0% Arlasolve | 6.7 |
| Azelaic Acid | 12.0% Ceraphyl | 6.1 |
| Azelaic Acid | 12.0% Collodion | 7.3 |
| Salicylic Acid | 12.0% Collodion | 5.0 |
| Experiment 3 | | |
| Azelaic acid | 12.0% Gel* | 6.7 |
| Salicylic Acid | 12.0% Collodion | 1.4 |

[1]Percent (w/w) of the active keratolytic agent in the designated vehicle.
*A description of this composition appears below with the title: 39.00% Arlasolve 200L and 00.50 Klucel HF.
[2]The mean KI of the combined vehicle control groups was less than 1 (range 0–1.0).

The number of guinea pigs tested in each Group was 3. Each experiment that analyzed the keratolytic effects of azelaic acid included a salicylic acid control.

The formulations shown in the above table were made by methods set forth in this specification or they were made by methods analogous to those set forth in this specication.

RESULTS OF IN VITRO STUDIES

The following sections summarize the results of the in vitro and in vivo studies that were performed to compare the effects of azelaic acid and SA on several cellular processes involved in keratinocyte differentiation. In these studies, morphological and biochemical events that occur during the processes of keratinocyte differentiation were analyzed. The analysis parameters included: 1. Cross-linked cell envelope formation, 2. Intracellular calcium flux, 3. Ultra-structural localization of calcium, 4. Apoptosis, 5. DNA synthesis, 6.

Desmosome degradation, and 7. Plasminogen activators expression.

These seven parameters are involved in terminal differentiation of keratinocytes, during the transition phase of epidermal development that results in the genesis of corneocytes for formation of the stratum corneum. Compounds that activate keratinocyte differentiation processes are believed to be more effective keratolytic agents. In most cases azelaic acid caused greater effects on the parameters listed above than did SA. However, the effects were not always toward increased differentiation.

Effects of Azelaic Acid and SA on Cross-linked Cellular Envelope Formation

Keratinocytes undergo terminal differentiation to become corneocytes, which form the stratum corneum layer of the epidermis. Corneocyte generation is a programmed press with recognized biochemical and morphological changes to the keratinocytes, that include: reorganization of intermediate filaments, accumulation of keratohyalin granules, production of certain lipids, and formation of the cellular envelope (CE). During the late stages of keratinocyte terminal differentiation, the highly insoluble, cross-linked protein CE is formed on the inner aspect of the cell's plasma membrane. Through the action of a plasma membrane associated transglutaminase, CE precursor proteins such as: loricrin, involucrin, and keratolinin are cross-linked by glutamyl)lysine bonds to form this specialized corneocyte structure. Since CE formation is a unique marker of terminally differentiated keratinocytes, an in vitro assay of CE induction was used to measure and compare the keratinocyte differentiation inducing potential of azelaic acid and SA.

The results of this study are presented. The scattering of light emitted at 340 nm was used as a relative measurement of CE formation. Data is presented as the mean±S.E.M. absorption ($A_{340}$) value for each of the test groups. CE were induced by treating SCC-9 cells (human squamous carcinoma cells) with SA. In comparison, about 3 times more CE were induced in cells treated with SA than CE induced by azelaic acid. Azelaic acid had no greater effect on CE formation than the control (ethanol at the same percentage of the CE formation buffer used to deliver the azelaic acid and SA into the buffer). These data indicate that azelaic acid, unlike SA, is not a potent stimulator of CE formation in SCC-9 cells.

Calcium ionophores, such as A23187, are capable of stimulating keratinocyte CE formation. This is consistent with the hypothesis that increased intracellular calcium levels trigger keratinocyte differentiation. It was believed that SA could stimulate CE formation by inducing intracellular calcium flux. Thus, a series of experiments were conducted to determine whether SA and azelaic acid had any effect on intracellular calcium levels in cultured keratinocytes or on the ultrastructural distribution of calcium within the epidermis of organ cultured skin tissue. The results of these studies are summarized in the next two sections.

A23187 is the antibiotic calcimycin with the formula $C_{29}H_{37}N_3O_6$ which is described on page 249, entry 1639 of Merck Index, 11th Edition, 1989, S. Budavari, Editor, Merck and Company, Rahway, N.J., and 4BrA23187 is a halogenated analog of A23187, available from Sigma Chemical Co. St. Louis, Mo.

Effects of Azelaic Acid and SA on Intracellular Calcium Levels

A fluorometric method was used to measure the relative levels of intracellular calcium in SCC-9 cells treated with various compounds. The cells were first labeled with a calcium chelating dye, 1-[2-amino-5-(6-carboxy indol-2yl)-phenoxy]-2-(2'-amino-5'-methyl-phenoxy)-ethane-N,N,N',N'-tetraacetoxymethyl ester (Indo-1AM). Indo-1AM is an ultraviolet (UV) excitable fluorochrome that emits increasing amounts of 407.6 nm light in a calcium concentration dependent manner. The results of this study indicate that A23187, SA and azelaic acid are capable of inducing increased intracellular calcium flux in SCC-9 cells. Azelaic acid induced a level of intracellular calcium flux that was about twice that induced by SA. In comparison, A23187, at a lower concentration, induced equivalent levels of intracellular calcium flux as SA. These compounds may act by either opening calcium ion channels or functioning as calcium ionophores. These data suggest, however, that intracellular calcium flux and CE formation are not necessarily dependent processes. Although only A23187 and SA stimulated CE formation.azelaic acid, A23187 and SA caused an increase in intracellular calcium levels, Effects of Azelaic Acid and SA on Ultrastructural Localization Of Calcium in Normal Human Skin A special tissue staining method was used to evaluate ultrastructural localization of calcium by TEM. Using this method electron dense calcium precipitates were visualized at ultrastructural sites of high calcium concentration. The results of this study were determined from photomicrographs. The distribution of calcium within a keratinocyte in the stratum spinosum of a piece of untreated, control skin was examined. Calcium was associated in aggregates that were evenly dispersed throughout the nuclear euchromatin. Calcium was also readily observed in the cytoplasm of this cell and extracellular compartment. A section of untreated control skin was taken at the level of the stratum granulosum. High concentrations of calcium were seen in the extracellular space along the cell borders and in association with the desmosomes.

In contrast, in keratinocytes of skin treated with azelaic acid, calcium was not detected by this method in the extracellular compartment, in association with desmosomes or in the stratum corneum. High concentrations of calcium were distributed throughout the nuclear euchromatin of keratinocytes from azelaic acid treated skin. In keratinocytes where the nucleus had condensed, high concentrations of calcium were seen in the vacant nuclear space. Calcium was also associated with the mitochondria. In addition calcium was seen in the cytoplasm in high concentration. There was no evidence of changes in desmosome adhesion in this tissue section.

In the stratum spinosum of skin treated with SA, the distribution of calcium was similar, but not identical, to that observed in azelaic acid treated skin. For example, there was very little calcium seen in either the extracellular compartment or associated with desmosomes. Unlike the effect of azelaic acid, SA treatment did not cause changes in the adhesion of desmosomes. Calcium in the nuclei of keratinocytes in skin treated with SA was highly concentrated within the heterochromatin. In this section two keratinocytes were observed. In one keratinocyte calcium was not detected in the euchromatin, in the other keratinocyte calcium was thinly dispersed in the euchromatin.

Collectively, these data demonstrate the variable effects of azelaic acid and SA on calcium localization within the skin. Changes in calcium distribution from the extracellular compartment to the nuclear compartment are believed to be linked to enhanced keratinocyte differentiation and desquamation, and these studies are therefore believed to clearly show that the effect of azelaic acid is greater than that of SA in causing these changes. The final two in vitro studies, summarized below, determined whether the effects on CE formation, intracellular calcium flux and ultrastructural calcium distribution correlated with corneocyte cell adhesion, that is, degradation of the desmosomes.

Effects of Azelaic Acid and SA on Apoptosis

Apoptosis is the programmed or gene-controlled process of cell death. It is believed be a factor in regulating normal differentiation of the skin and other tissues and it is believed to affect desquamation. Apoptosis is believed to be a part of the normal transition of keratinocytes to corneocytes that occurs in the stratum granulosum, a process that is altered in corns. Apoptosis induction experiments were performed in vitro using cultured normal human epidermal keratinocytes (NHEK) or squamous cell carcinoma cells (SCC-9). The following parameters were used for these experiments: $3 \times 10^6$ cells were treated for four days with 10 mM of the test compound in medium containing a final concentration of 1.5 mM calcium. Apoptosis was determined by measuring DNA fragmentation utilizing agarose gel electrophoresis. A subjective scale for measuring apoptosis called the apoptosis factor was used to score the results from the gel tests. This subjective scale used A23187, a calcium ionophore, as the positive control; thus all of the test compounds were compared to the effects of A23187 on inducing DNA fragmentation. The positive control, A23187 has an apoptosis factor of 4. In comparison, azelaic acid has an apoptosis factor of 3 compared to a relative apoptosis factor of 1 for SA. Thus, azelaic acid causes a greater amount of DNA fragmentation in this model than does SA.

Effects of Azelaic Acid and SA on Inhibition of DNA Synthesis

Inhibition of DNA synthesis in keratinocytes is believed to play a role in treating hyperkeratotic conditions such as psoriasis, corns and callus. Inhibiting keratinocyte proliferation could aid in reversing abnormal hyperproliferation in these tissues. Experiments were conducted on third passage NHEK cells treated with test compounds to determine inhibition of DNA synthesis. Tritiated thymidine uptake inhibition in treated versus control cells was used to measure DNA synthesis inhibition. Triplicate wells of NHEK cells grown in 6-well trays were used per treatment group. The cells were simultaneously pulsed with $^3$H-thymidine and the test compound and allowed to incubate overnight (18 hours). Following this treatment, the cells were harvested and $^3$H-thymidine taken up by the cells was measured by liquid scintillation counting. At a concentration of 10 mM azelaic acid caused a 77.2% inhibition of $^3$H-thymidine uptake compared to the vehicle control, while SA caused a 50% inhibition versus control. When both compounds were tested at 20 mM concentrations, azelaic acid caused a 93% inhibition and SA caused a 50% decrease in proliferation in NHEK cells by this in vitro method.

Effect of Azelaic Acid and SA on the Expression and Distribution of Desmosomal Proteins, Desmoglein and Desmoplakin, in the Epidermis of Organ Cultured Normal Human Skin Desmosomes are intercellular junctions that provide cell-to-cell adhesion and anchorage for intracellular keratin tonofilaments. They consist of at least two classes of proteins called desmoplakins and desmogleins. Desmoplakins are strictly plasma membrane associated intracellular proteins. Desmogleins extend from the plasma membrane plaque across the extracellular space where they associate with the desmogleins of an adjacent cell. Disruption of the desmosomes leads to acantholysis and skin sloughing. To investigate the possibility that keratics may alter desmosome adhesion, a skin organ culture model was developed.

For these studies, pieces of normal human skin were placed in organ culture. They were incubated for 24 hours in medium containing azelaic acid or SA. The skin samples were then processed for indirect immunoperoxidase staining using monoclonal antibodies against human desmoglein (DG) and desmoplakin as the primary antibodies. Disruption or degradation of this protein, as measured by immunoperoxidase staining intensity, would significantly weaken the desmosomes. The results of this study were seen in three photomicrographs.

It is readily apparent that DG is expressed throughout the stratum spinosum layer of control skin, as well as skin treated with SA and azelaic acid. There is less anti-DG staining in the basal and parabasal areas in SA treated skin compared to that of untreated and azelaic acid treated skin. Anti-DG staining in azelaic acid treated skin is not significantly less than that in the control skin. These observations are consistent with the observed ultrastructural changes to desmosomes presented in the TEM photomicrographs. In contrast to the observed changes to DG, both azelaic acid and SA caused an equivalent and marked decrease in the expression of desmoplakin. Alterations to or destruction of the desmosome complexes expressed by keratinocytes would greatly affect the strength of the intercellular adhesion of the epidermis. Evidence that SA, and to a lesser extent azelaic acid, treatment can alter these extracellular structures is a strong indication that these compounds may be very effective keratolytic agents for corn removal without causing extensive tissue damage as demonstrated by light microscopy of H&E stained tissue sections.

Effects of Azelaic Acid and SA on Plasminogen Activator Expression

As normal epidermal keratinocytes differentiate, they migrate vertically to form stratified epithelium. Proteinases are believed to play a role in the epidermal differentiation press. Proteolytic enzymes are activated by increased calcium which destroy cellular organelles and cleave proteins such as desmosomes.

The active proteolytic enzyme plasmin, is produced when plasminogen activators cleave plasminogen. Plasminogen activators are serine proteinases that are classified into two types, tissue type plasminogen activator (tPA) and urokinase type plasminogen activator (uPA). Fibrinolysis is believed to be regulated by tPA, whereas, uPA is an important mediator of pericellular matrix degradation. It has been shown that uPA is indicated in proteolysis of intercellular keratinocyte proteins. Increasing calcium concentration to 1 mM causes uPA to redistribute along cell-cell borders. This suggests that uPA may be involved in regulation of epidermal adhesion through proteolysis. Furthermore, a biologically controlled PA cascade appears to help regulate epidermal differentiation in skin.

The activity of tPA and uPA is regulated by plasminogen activator inhibitors. Plasminogen inhibitors fall into two major types, plasminogen inhibitor type 1 (PAI-1) and plasminogen inhibitor type 2 (PAI-2). Both PAI-1 and PAI-2 are able to inhibit tPA and uPA.

Throughout the suprabasal layers of the normal epidermis there are small amounts of tPA. Thus, the distribution of tPA in the superficial layers implies an epidermal differentiation function. Based on this hypothesis, in tissue where the tPA levels are biologically imbalanced, one would expect abnormal epidermal differentiation. In studies of psoriasis, blistering diseases and other cutaneous disorders, tPA is found in the suprabasal layer. We have shown that such an imbalance exists in untreated corn tissue. In our studies untreated corn has a decreased amount of tPA and increased level of PAI-2 when compared with normal epidermis. This is consistent with the hypothesis that a corn is the result of abnormal differentiation. SA treated corns show tPA and PAI-2 levels comparable to normal epidermis. These results suggest that SA causes an increase in the levels of both tPA and PA in corn tissue to that of normal epidermis.

In vitro studies on SCC-9 cells were conducted to determine the effects of azelaic acid and SA on the gene expression of tPA, uPA and their inhibitors (PAI-1 and PAI-2). SCC-9 cells were treated with 5 mM azelaic acid for 48 hours. Total RNA was extracted and processed for polymerase chain reaction (PCR) analysis to amplify genes for the plasminogen activators and their inhibitors. Test samples with appropriate controls from the PCR analysis were run on agarose gels to determine the level of gene expression. There was a slight down-regulation of tPA gene transcripts in cells treated with azelaic acid compared to controls. No other genes appeared to be affected by treatment with azelaic acid. In contrast, SA was less effective in modulating the gene expression of either PAs or their inhibitors. In summary, azelaic acid was able to cause a slight down-regulation of tPA expression by SCC-9 cells when compared to SA.

Conclusions from the in Vitro Studies

The results of our in vitro studies to define the mechanisms of action of SA are consistent with our hypothesis that keratolytic activity is associated with enhanced keratinocyte differentiation. We showed that SA triggers CE formation, causes increased intracellular calcium levels, affects ultrastructural localization of cellular calcium, and induces apoptosis. In the organ cultured human skin model, SA was found to cause increased proteolysis of desmosomes in normal human skin and corn tissue. These processes are known to be involved in the normal differentiation of keratinocytes to corneocytes. Furthermore, these transitional steps toward the formation of the stratum corneum result in regulated desquamation of corneocytes from the surface of the epidermis.

In comparative studies, we showed that azelaic acid, like SA, exerted important effects on certain keratinocyte differentiation processes. For example, azelaic acid strongly effected, intracellular calcium flux, ultrastructural distribution of calcium and DNA fragmentation. More importantly, these studies showed that various keratinocyte differentiation processes may be triggered independently, for example, azelaic acid, unlike SA, caused increased intracellular calcium levels without CE formation. On the other hand, SA caused both increased intracellular calcium levels and CE formation.

Conclusions from the in Vitro Studies

In comparative studies, we showed that azelaic acid, like SA, exerted important effects on certain keratinocyte differentiation processes. For example, azelaic acid strongly effected, intracellular calcium flux, ultrastructural distribution of calcium and DNA fragmentation. More importantly, these studies showed that various keratinocyte differentiation processes may be triggered independently, e.g., azelaic acid, unlike SA, caused increased intracellular calcium levels without CE formation. On the other hand, SA caused both increased intracellular calcium levels and CE formation.

Summary of Histopathology Study

Photographs of gross epidermal changes and higher KI scores indicated that 12% azelaic acid had stronger keratolytic effects on guinea pig footpad callus removal than did 12% SA.

Conclusions from the Animal Studies

The results of the GPFAs indicate that azelaic acid has stronger keratolytic action than SA for mediating guinea pig footpad callus removal. This finding is consistent with the results of our in vitro studies, summarized above, showing azelaic acid was significantly more effective than SA in stimulating certain processes involved in keratinocyte differentiation. Interestingly, the stronger keratolytic activity of azelaic acid did not result in any adverse tissue damage beyond that which is acceptable for approved keratolytic agents, such as SA. Therefore, application of azelaic acid to hyperkeratinized human corn tissue does not appear to present a safety risk above that associated with SA.

Preferred ingredients of compositions of the invention fall within the following ranges:

| Component | Percentage of Formula % (weight/weight) |
| --- | --- |
| AZA | 4–20 |
| EtOH | 20–60 |
| Arlasolve 200 L | 30–50 |
| Klucel HF | 0.3–5 |

Additional compositions of the invention which have been prepared are as follows:

| Liquid Formula for Azelaic Acid. | |
| --- | --- |
| Component | Percentage of formula % (weight/weight) |
| azelaic acid | 12.00 |
| Acetone | 10.00 |
| Flexible collodion (USP) | 72.95 |
| Balsam fir (Oregon) | 5.00 |
| β-Carotene HSE 22% in vegetable oil | 0.05 |

The Azelaic Acid formula was prepared as follows:

1) Balsam fir (Oregon) was mixed with acetone in a suitable vessel.
2) Flexible collodion, USP, was added to the solution prepared in step 1 and thoroughly mixed.
3) Azelaic Acid was added to the solution prepared in step 2.
4) The composition from step 3 was thoroughly mixed until the Azelaic acid was completely dissolved.
5) The composition made in step 5 was then transferred to appropriate containers for storage at room temperature ranging from about 22° to about 27° C.

The liquid formula for azelaic acid, below, was prepared in a similar way to the formulation for azelaic acid set forth just above.

| Component | Percentage of Formula % (weight/weight) |
|---|---|
| Azelaic Acid | 12.00 |
| Balsam Fir (Oregon) | 5.0 |
| Acetone | 10.0 |
| Flexible Collodion, USP | q.s. 100.0 |

| Ucare Polymer Gel Formulation | |
|---|---|
| AZA | 12% |
| EtOH | 48% |
| Ucare Polymer Gel Base* | 40% |

As used herein AZA means azelaic acid.
*Ucare Polymer Gel Base was 63.5% water; 1.5% Ucare Polymer JR; and 35% ethanol.

The Ucare Polymer Gel Formulation was prepared as follows:

1) AZA and ethanol were mixed in a suitable container.
2) This mixture was heated, until all of the AZA had dissolved. During the heating, care was taken to keep the mixture below 80° C.
3) Ucare Polymer Gel base was added to the composition in step 2.
4) The composition in step 3 was mixed thoroughly.
5) The composition in step 4 was transferred to an appropriate container for storage at room temperature ranging from about 22° to about 27° C.

Ucare Polymer Gel has the name Ucare Polymer JR-M-Poly quaternium-10. It is a polymeric quaternium ammonium salt of hydroxyethylcellulose reacted with a trimethylammonium substituted epoxide.

| Arlasolve 200 L Formulation | |
|---|---|
| Component | Percentage of Formula % (weight/weight) |
| AZA | 12% |
| EtOH | 48% |
| Arlasolve 200 L | 40% |

The Arlasolve 200L Formulation was prepared as follows:

1) AZA and ethanol were mixed in a suitable container.
2) This mixture was heated, until all of the AZA had dissolved. During the heating, care was taken to keep the mixture below 80° C.
3) Arlasolve 200L was added to the composition in step 2.
4) The composition in step 3 was mixed thoroughly.
5) The composition in step 4 was transferred to an appropriate container for storage at room temperature ranging from about 22° to about 27° C.

Arlasolve 200L has the full name Arlasolve 200L-Isoceteth-20. It is a polyethylene glycol ether of isocetyl alcohol and it has the chemical 25 formula: $C_{16}H_{33}(OCH_2CH_2)_nOH$ where n has an average value of 20.

| Ceraphyl 230 Formulation | |
|---|---|
| Component | Percentage of Formula % (weight/weight) |
| AZA | 12% |
| EtOH | 48% |
| Ceraphyl 230 | 40% |

The Ceraphyl 230 Formulation was prepared as follows:

1) AZA and ethanol were mixed in a suitable container.
2) This mixture was heated, until all of the AZA had dissolved. During the heating, care was taken to keep the mixture below 80° C.
3) Ceraphyl 230 was added to the composition in step 2.
4) The composition in step 3 was mixed thoroughly.
5) The composition in step 4 was transferred to an appropriate container for storage at room temperature ranging from about 22° to about 27° C.

Ceraphyl 230 is a diester of isopropyl alcohol and adipic acid and it is called diisopropyl adipate. It has the empirical formula: $C_{12}H_{22}O_4$ and the chemical formula:

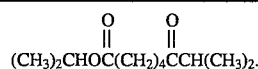

$$(CH_3)_2CHOC(CH_2)_4CCH(CH_3)_2$$
with two C=O groups.

| Klucel HF Formulation | |
|---|---|
| Component | Percentage of Formula % (weight/weight) |
| AZA | 12% |
| EtOH | 48% |
| Klucel HF Base* | 40% |

*Klucel HF Base was 65% ethanol; 1.5% Klucel HF; and 33.5% water.

The Klucel HF Formulation was prepared as follows:

1) AZA and ethanol were mixed in a suitable container.
2) This mixture was heated, until all of the AZA had dissolved. During the heating, care was taken to keep the mixture below 80° C.
3) Klucel HF was added to the composition in step 2.
4) The composition in step 3 was mixed thoroughly.
5) The composition in step 4 was transferred to an appropriate container for storage at room temperature ranging from about 22° to about 27° C.

The full name for Klucel HF is Klucel HF-Hydroxypropylcellulose and it is a propylene glycol ether of cellulose.

| "88" Vehicle Formulation | |
|---|---|
| Component | Percentage of Formula % (weight/weight) |
| AZA | 12% |
| EtOH | 48% |
| "88" Vehicle* | 40% |

*The "88" Vehicle was 74% ethanol; 14% propylene glycol; and 12% water.

The "88" Vehicle Formulation was prepared as follows:

1) AZA and ethanol were mixed in a suitable container.
2) This mixture was heated, until all of the AZA had dissolved. During the heating, care was taken to keep the mixture below 80° C.
3) "88" Vehicle was added to the composition in step 2.
4) The composition in step 3 was mixed thoroughly.

5) The composition in step 4 was transferred to an appropriate container for storage at room temperature ranging from about 22° to about 27° C.

| Regulaid Formulation | |
|---|---|
| Component | Percentage of Formula % (weight/weight) |
| AZA | 12% |
| EtOH | 28% |
| Regulaid | 20 |
| Ucare Polymer Gel Base* | 40% |

*Ucare Polymer Gel Base was as described above.

The Regulaid Formulation was prepared as follows:

1) AZA, ethanol and Regulaid were mixed in a suitable container.
2) This mixture was heated, until all of the AZA had dissolved. During the heating, care was taken to keep the mixture below 80° C.
3) Ucare Polymer Gel Base was added to the composition in step 2.
4) The composition in step 3 was mixed thoroughly, and heated to less than 80° C.
5) The composition in step 4 was transferred to an appropriate container for storage at room temperature ranging from about 22° to about 27° C.

Regulaid is a proprietary composition which is a blend of polyoxyethylene-polypropoxy propanol, dihydroxy propane and alkyl 2ethoxyethanol. Regulaid is made by Colloidal Products, Inc. of 2655 Le Jeune Road Ste 2, Miami Fla. 33134.

| 2-HEM Formulation | |
|---|---|
| Component | Percentage of Formula % (weight/weight) |
| AZA | 12% |
| EtOH | 28% |
| 2-HEM | 20 |
| Klucel-HF Base* | 40% |

*See above description for the Klucel-HF Base

The 2-HEM Formulation was prepared as follows:

1) AZA and ethanol were mixed in a suitable container.
2) This mixture was heated, until all of the AZA had dissolved. During the heating, care was taken to keep the mixture below 80° C.
3) 2-HEM was added to the composition in step 2.
4) The composition in step 3 was mixed thoroughly, and heated to less than 80° C.
5) Klucel-HF was added to the composition in step 4 and mixed thoroughly.
6) The composition in step 5.was transferred to an appropriate container for storage at room temperature ranging from about 22° to about 27° C.

As used herein, 2-HEM refers to 2-hydroxyethyl methacrylate.

| Ucare Polymer Gel Formulation | |
|---|---|
| Component | Percentage of Formula % (weight/weight) |
| AZA | 4% |
| EtOH | 48% |
| Ucare Polymer Gel Base* | 48% |

* See the above description for the Ucare Polymer Gel Base

As used herein AZA means azelaic acid.

The Ucare Polymer Gel Formulation was prepared as follows:

1) AZA and ethanol were mixed in a suitable container.
2) This mixture was heated, until all of the AZA had dissolved. During the heating, care was taken to keep the mixture below 80° C.
3) Ucare Polymer Gel base was added to the composition in step 2.
4) The composition in step 3 was mixed thoroughly.
5) The composition in step 4 was transferred to an appropriate container for storage at room temperature ranging from about 22° to about 27° C.

| Ucare Polymer Gel Formulation | |
|---|---|
| Component | Percentage of Formula % (weight/weight) |
| AZA | 20% |
| EtOH | 40% |
| Ucare Polymer Gel Base* | 40% |

* See the above description for the Ucare Polymer Gel Base

As used herein AZA means azelaic acid

The Ucare Polymer Gel Formulation was prepared as follows:

1) AZA and ethanol were mixed in a suitable container.
2) This mixture was heated, until all of the AZA had dissolved. During the heating, care was taken to keep the mixture below 80° C.
3) Ucare Polymer Gel base was added to the composition in step 2.
4) The composition in step 3 was mixed thoroughly.
5) The composition in step 4 was transferred to an appropriate container for storage at room temperature ranging from about 22° to about 27° C.

| Ucare Polymer Gel Formulation | |
|---|---|
| Component | Percentage of Formula % (weight/weight) |
| Suberic acid | 12% |
| EtOH | 48% |
| Ucare Polymer Gel Base* | 40% |

* See the above description for the Ucare Polymer Gel Base

The Ucare Polymer Gel Formulation was prepared as follows:

1) Suberic acid and ethanol were mixed in a suitable container.
2) This mixture was heated, until all of the Suberic acid had dissolved. During the heating, care was taken to keep the mixture below 80° C.
3) Ucare Polymer Gel base was added to the composition in step 2.

4) The composition in step 3 was mixed thoroughly.

5) The composition in step 4 was transferred to an appropriate container for storage at room temperature ranging from about 22° to about 27° C.

The following is the most preferred composition of the invention.

| 39.00% Arlasolve 200L and 00.50 Klucel HF. | |
|---|---|
| Component | Percentage of Formula % (weight/weight) |
| Part A | |
| AZA | 12.00% |
| EtOH | 48.50% |
| Part B | |
| Arlasolve 200L | 39.00% |
| Klucel HF | 00.50% |

1) AZA was added to the EtOH of part A and mixed until dissolved, by swirling in a glass bottle with a tight closure. Evaporation of EtOH was avoided as much as possible.

2) The ariasolve of part B was placed into a glass beaker large enough to contain the entire batch. The Klucel of part B was added and mixed with a small mixer until well dispersed.

3) While mixing the mix at step 2, the mix of step 1 was added and mixed until uniform and the Klucel was completely hydrated.

4) The resulting mixture was stored in closed containers to avoid the evaporation of the EtOH.

As used herein and throughout the specification and the claims EtOH refers to ethanol, 190 proof, USP.

What is claimed is:

1. A topical composition in gel form, consisting essentially of a 7 to 13 carbon dicarboxylic acid or a corresponding salt or ester thereof in a range of about 4 to about 64% and a pharmaceutically acceptable carrier material.

2. A composition in accordance with claim 1 wherein the 7 to 13 carbon dicarboxylic acid is selected from the group consisting of $HO_2C(CH_2)_7CO_2H$, $HO_2C(CH_2)_8CO_2H$, $HO_2C(CH_2)_9CO_2H$, $HO_2C(CH_2)_{10}CO_2H$, $HO_2C(CH_2)_{11}CO_2H$, $HO_2C(CH_2)_6CO_2H$, $HO_2C(CH_2)_5CO_2H$, $HO_2C(CH_2)_2CHCH_3$ $(CH_2)_3CO_2H$, $HO_2C(CH_2)_6(CHCH_3)$ $CO_2H$, and

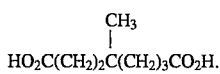

$$HO_2C(CH_2)_2C(CH_3)(CH_2)_3CO_2H.$$

3. A composition in accordance with claim 2 wherein the 7 to 13 carbon dicarboxylic acid is azelaic acid.

4. A composition in accordance with claim 3 wherein the azelaic acid is in a range of about 8 to about 40% (weight/weight).

5. A composition in accordance with claim 4 wherein the azelaic acid is in a range of about 4 to about 20% (weight/weight).

6. A composition in accordance with claim 1 wherein the pharmaceutically acceptable carrier material is selected from the group consisting of polyethylene glycol 1000 isocetyl ether, and cellulose, 2-hydroxypropyl ether; a mixture of 63.5% double distilled water, 1.5% Ucare Polymer and 35.0% ethanol USP; cellulose, 2-hydroxypropyl ether; and 2-hydroxyethyl methacrylate; and cellulose, 2-hydroxypropyl ether.

7. A topical composition in accordance with claim 6 consisting essentially of on a weight/weight basis:

| Component | Percent of Formula % (weight/weight) |
|---|---|
| AZA | 4–20 |
| EtOH | 20–60 |
| polyethylene glycol 1000 isocetyl ether | 30–50 |
| cellulose, 2-hydroxypropyl ether | 0.3–5. |

8. A method for removing corns and calluses which comprises topically administering a therapeutically effective amount of a composition defined in claim 1.

9. A topical composition in accordance with claim 1 consisting essentially of on a weight/weight basis:

| Component | Percent of Formula % (weight/weight) |
|---|---|
| AZA | 12% |
| EtOH | 47% |
| polyethylene glycol 1000 isocetyl ether | 39% |
| cellulose, 2-hydroxypropyl ether | 2%. |

10. A topical composition in accordance with claim 1 consisting essentially of on a weight/weight basis:

| Component | Percentage of Formula % (weight/weight) |
|---|---|
| Part A | |
| AZA | 12.00% |
| EtOH | 48.50% |
| Part B | |
| polyethylene glycol 1000 isocetyl ether | 39.00% |
| cellulose, 2-hydroxypropyl ether | 00.50%. |

11. A topical composition in accordance with claim 1 consisting essentially of on a weight/weight basis:

| Component | Percentage of Formula % (weight/weight) |
|---|---|
| AZA | 12% |
| EtOH | 48% |
| a mixture of 63.5% double distilled water, 1.5% Ucare Polymer and 35.0% ethanol USP; | 40%. |

12. A topical composition in accordance with claim 1 consisting essentially of on a weight/weight basis:

| Component | Percentage of Formula % (weight/weight) |
|---|---|
| AZA | 12% |
| EtOH | 48% |
| cellulose, 2-hydroxypropyl ether | 40%. |

13. A topical composition in accordance with claim 1 consisting essentially of on a weight/weight basis:

| Component | Percentage of Formula % (weight/weight) |
|---|---|
| AZA | 12% |
| EtOH | 28% |
| a mixture of polyoxyethylene-polypropoxypropanol, dihydroxy propane and alkyl 2-ethoxyethanol cellulose, 2-hydroxypropyl ether; | 20 40%. |

14. A topical composition in accordance with claim 1 consisting essentially of on a weight/weight basis:

| Component | Percentage of Formula % (weight/weight) |
|---|---|
| AZA | 12% |
| EtOH | 28% |
| 2-hydroxyethyl methacrylate | 20 |
| a mixture of 65.0% ethanol USP 1.5% Klucel HF and 33.5% double distilled water | 40%. |

15. A liquid topical composition consisting essentially of a collodion film forming vehicle, and a 7 to 13 carbon dicarboxylic acid or a corresponding pharmaceutically acceptable salt or ester thereof in a range of about 4 to about 64%.

16. A composition in accordance with claim 15 wherein the film forming vehicle is Flexible Collodion, USP.

17. A topical composition in accordance with claim 15 consisting essentially of on a weight/weight basis:

| Component | Percentage of formula % (weight/weight) |
|---|---|
| azelaic acid | 12.00 |
| Acetone | 10.00 |
| Flexible collodion (USP) | 72.95 |
| Balsam fir (Oregon) | 5.00 |
| β-Carotene HSE 22% in vegetable oil | 0.05 |

18. A topical composition in accordance with claim 15 consisting essentially of a weight/weight basis:

| Component | Percentage of Formula % (weight/weight) |
|---|---|
| AZA | 12.00 |
| Balsam Fir (Oregon) | 5.0 |
| β-Carotene, 22% in Vegetable Oil | 0.01 |

| Component | Percentage of Formula % (weight/weight) |
|---|---|
| Acetone | 10.0 |
| Flexible Collodion, USP q.s. | 100.0. |

19. A liquid alcoholic topical composition consisting essentially of a pharmaceutically acceptable carrier material, and a 7 to 13 carbon dicarboxylic acid or a corresponding pharmaceutically acceptable salt or ester thereof in a range of about 4 to about 64%.

20. A composition in accordance with claim 19, wherein a pharmaceutically acceptable carrier material is selected from the group consisting of polyethylene glycol 1000 isocetyl ether; bis(1-methylethyl)hexandioate; and a mixture of 74% ethanol, USP, 14% propylene glycol, and 12% double distilled water.

21. A topical composition in accordance with claim 19 consisting essentially of on a weight/weight basis:

| Component | Percentage of Formula % (weight/weight) |
|---|---|
| AZA | 12% |
| EtOH | 48% |
| Polyethylene glycol 1000 isocetyl ether | 40%. |

22. A topical composition in accordance with claim 19 consisting essentially of on a weight/weight basis:

| Component | Percentage of Formula % (weight/weight) |
|---|---|
| AZA | 12% |
| EtOH | 48% |
| Bis(1-methylethyl)hexandioate | 40%. |

23. A topical composition in accordance with claim 19 consisting essentially of on a weight/weight basis:

| Component | Percentage of Formula % (weight/weight) |
|---|---|
| AZA | 12% |
| EtOH | 48% |
| a mixture of 74% ethanol, USP, 14% propylene glycol, and 12% double distilled water | 40%. |

* * * * *